(12) United States Patent
Kyle, Jr.

(10) Patent No.: US 7,121,280 B2
(45) Date of Patent: Oct. 17, 2006

(54) MEDICAL DEVICES AND METHODS OF SELECTIVELY AND ALTERNATELY ISOLATING BRONCHI OR LUNGS

(75) Inventor: Garry Wayne Kyle, Jr., Flower Mound, TX (US)

(73) Assignee: Cook Critical Care Incorporated, Bloomington, IN (US)

( * ) Notice: Subject to any disclaimer, the term of this patent is extended or adjusted under 35 U.S.C. 154(b) by 65 days.

(21) Appl. No.: 11/074,543

(22) Filed: Mar. 8, 2005

(65) Prior Publication Data

US 2005/0205097 A1 Sep. 22, 2005

Related U.S. Application Data

(60) Provisional application No. 60/553,763, filed on Mar. 17, 2004.

(51) Int. Cl.
*A61M 16/00* (2006.01)

(52) U.S. Cl. .............................. 128/207.14; 128/207.16

(58) Field of Classification Search ........... 128/200.24, 128/200.26, 207.14, 207.15, 207.16, 207.18, 128/207.29, 912; 604/541, 35, 164.13, 164.03, 604/102.01, 102.02, 102.03; 623/23.65
See application file for complete search history.

(56) References Cited

U.S. PATENT DOCUMENTS

| | | | |
|---|---|---|---|
| 2,210,744 A | 8/1940 | Winder | |
| 4,022,219 A * | 5/1977 | Basta | 128/207.14 |
| 4,231,365 A | 11/1980 | Scarberry | |
| 4,248,221 A | 2/1981 | Winnard | |
| 4,449,523 A | 5/1984 | Szachowicz et al. | |
| 4,453,545 A | 6/1984 | Inoue | |
| 4,573,460 A | 3/1986 | Szachowicz et al. | |
| 4,688,568 A | 8/1987 | Frass et al. | |
| 4,819,664 A | 4/1989 | Nazari | |
| 5,056,515 A * | 10/1991 | Abel | 128/207.15 |
| 5,067,496 A | 11/1991 | Eisele | |
| 5,285,778 A | 2/1994 | Mackin | |
| 5,315,992 A | 5/1994 | Dalton | |
| 5,499,625 A | 3/1996 | Frass et al. | |

(Continued)

FOREIGN PATENT DOCUMENTS

DE 10109935 A1 11/2001

(Continued)

OTHER PUBLICATIONS

"Cook Slide Presentation—Arndt Endobronchial Blocker," Cook Interventional Critical Care Products, www.cookgroup.com, 2002, pp. 1-2.

(Continued)

*Primary Examiner*—Teena Mitchell
(74) *Attorney, Agent, or Firm*—Brinks Hofer Gilson & Lione

(57) ABSTRACT

Devices, kits, and methods for selectively and alternately isolating one of a pair of bronchi or lungs are provided. A main body has proximal and distal ends defining a lumen, a side port and opening formed near the distal end. An insert having first and second ends, and an aperture located near the second end, is configured to have the second end placed in the main body lumen. The insert aperture permits passageway to at least one of the main body side port or distal opening, while an exchangeable insert permits passageway to the other main body side port or opening, or optionally one insert moves between first and second positions to selectively and alternately permit passageway to the one or other main body side port or opening. Kits and methods are provided for selectively and alternately isolating one of a pair of bronchi or lungs.

29 Claims, 7 Drawing Sheets

U.S. PATENT DOCUMENTS

| | | | |
|---|---|---|---|
| 5,588,424 | A | 12/1996 | Insler et al. |
| 5,771,888 | A | 6/1998 | Keim |
| 5,954,636 | A | 9/1999 | Schwartz et al. |
| 6,609,521 | B1 | 8/2003 | Belani et al. |
| 6,722,367 | B1 * | 4/2004 | Blom .................... 128/207.14 |
| 2001/0054425 | A1 | 12/2001 | Bertram |
| 2002/0185135 | A1 | 12/2002 | Amar |

FOREIGN PATENT DOCUMENTS

| | | |
|---|---|---|
| GB | 2168256 A | 6/1986 |
| WO | WO 99/45990 | 9/1999 |

OTHER PUBLICATIONS

"Arndt Endobronchial Blocker—Suggested Instructions for Use," Cook, 2001, pp. 1-9.

"Lung Isolation Techniques," Peter Slinger, MD, on or before Oct. 29, 2002, http://www.anesthesia.org/winterlude/w197/W_LungIsolation.html, pp. 1-7.

"Insertion of a Double Lumen," W. John Russel, May 17, 2000, http://www.usyd.edu.au/su/anaes/lectures/dlt.htlm, pp. 1-2.

"Managing a Patient with Hemoptysis," Irawan Susanto, M.D., Journal of Bronchology, vol. 9, No. 1, Jan. 2002, pp. 40-45.

"Arndt Endobronchial Blocker Set," Cook Critical Care Products, www.cookgroup.com, 2001, pp. 1-6.

"Single Lung Ventilation in Children Using a New Paediatric Bronchial Blocker," Gregory B. Hammer, M.D., T. Kyle Harrison, M.D., Luca A. Vricella, M.D., Michael D. Black, M.D., and Elliot J. Krane, M.D., Paediatric Anaesthesia, 2002, pp. 69-72.

"A New Technique for Lung Isolation in Acute Thoracic Trauma," Hilary P. Grocott, M.D., FRCPC, Garrett Scales, M.D., David Schinderle, M.D., and Kathryn King, M.D., Journal of Trauma, vol. 49, No. 5, Nov. 2000, pp. 940-942

"One-Lung Ventilation When Intubation is Difficult—Presentation of a New Endobronchial Blocker," G.A. Arndt, S.T. DeLessio, P.W. Kranner, W. Orzepowski, B. Ceranski, and B. Valtysson, Acta Anaesthesiol Scand, 1999, pp. 356-358.

"Single-Lung Ventilation in a Critically III Patient Using a Fiberoptically Directed Wire-Guided Endobronchial Blocker," George A. Arndt, M.D., Paul W. Kranner, M.D., Deborah A. Rusy, M.D., Robert Love, M.D., Anesthesiology, vol. 90, No. 5, May 1999, pp. 1484-1486.

"Wire-Guided Endo-Bronchial Blockade in a Patient with a Limited Mouth Opening," George A. Arndt, M.D., Samantha Buchika, M.D., Paul W. Kranner, M.D., and Stephen T. DeLessio, M.D., Can J Anesth, 1999, 46:1, pp. 87-89.

"Reversal of Hypoxemia Using Insufflation of Oxygen During One-Lung Ventilation with a Wire-Guided Endobronchial Blocker," Journal of Cardiothoracic and Vascular Anesthesia, vol. 15, No. 1, Feb. 2001, p. 144.

First Experience with Fiberoptically Directed Wire-Guided Endobronchial Blockade in Severe Pulmonary Bleeding in an Emergency Setting, Barbara Kabon, M.D., Barbara Waltl, M.D., Johannes Leitgeb, M.D., Stephan Kapral, M.D., and Michael Zimpfer, M.D., Chest, vol. 120, Oct. 2001, p. 1399-1402.

"Univent—The New Concept for One Lung Anesthesia," Phycon Univent, Fuji Systems Corporation, (prior to Mar. 17, 2004), pp. 1-4.

Search Report and Written Opinion dated Jun. 3, 2005, for International Application No. PCT/US2005/007533.

* cited by examiner

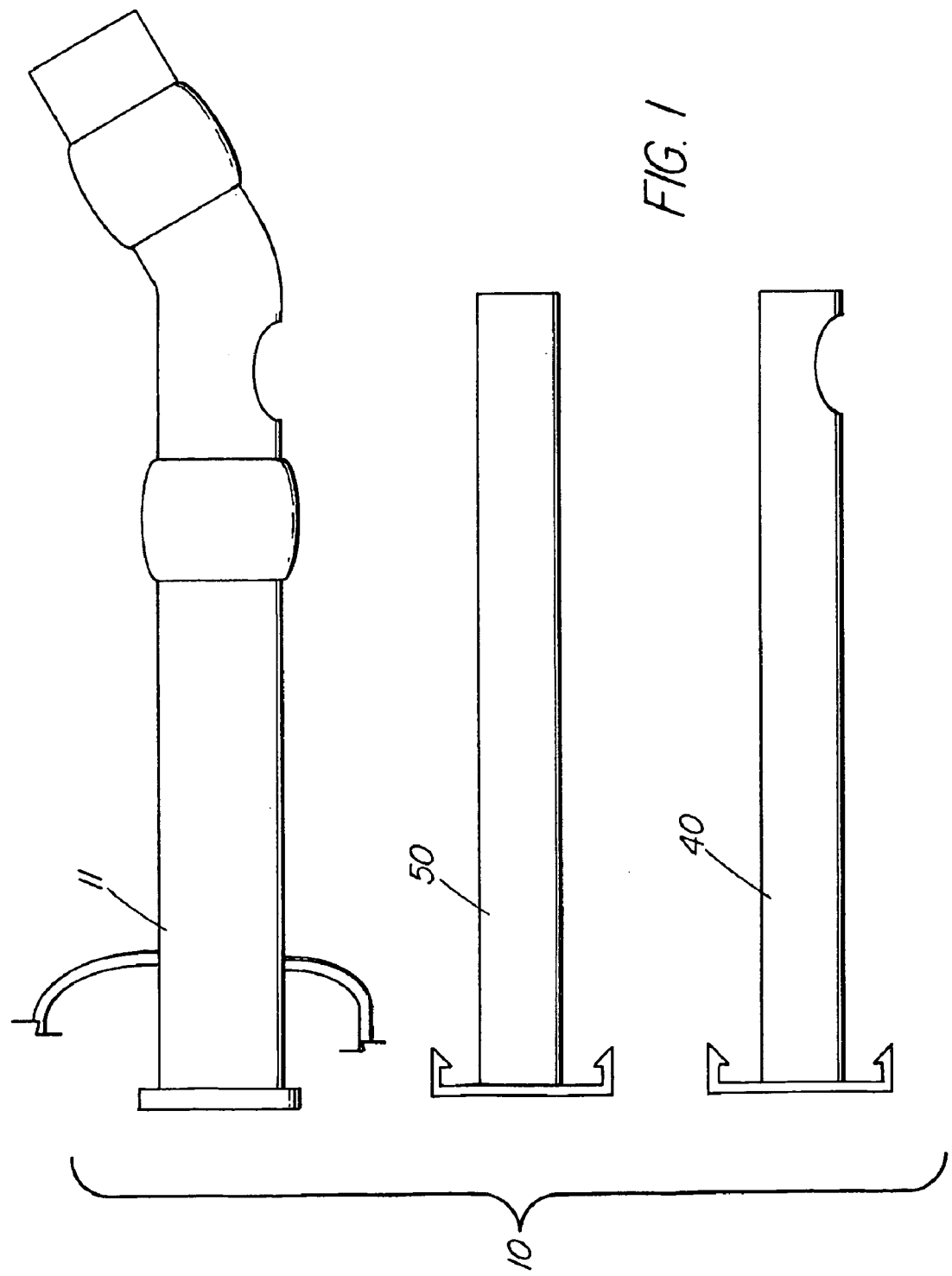

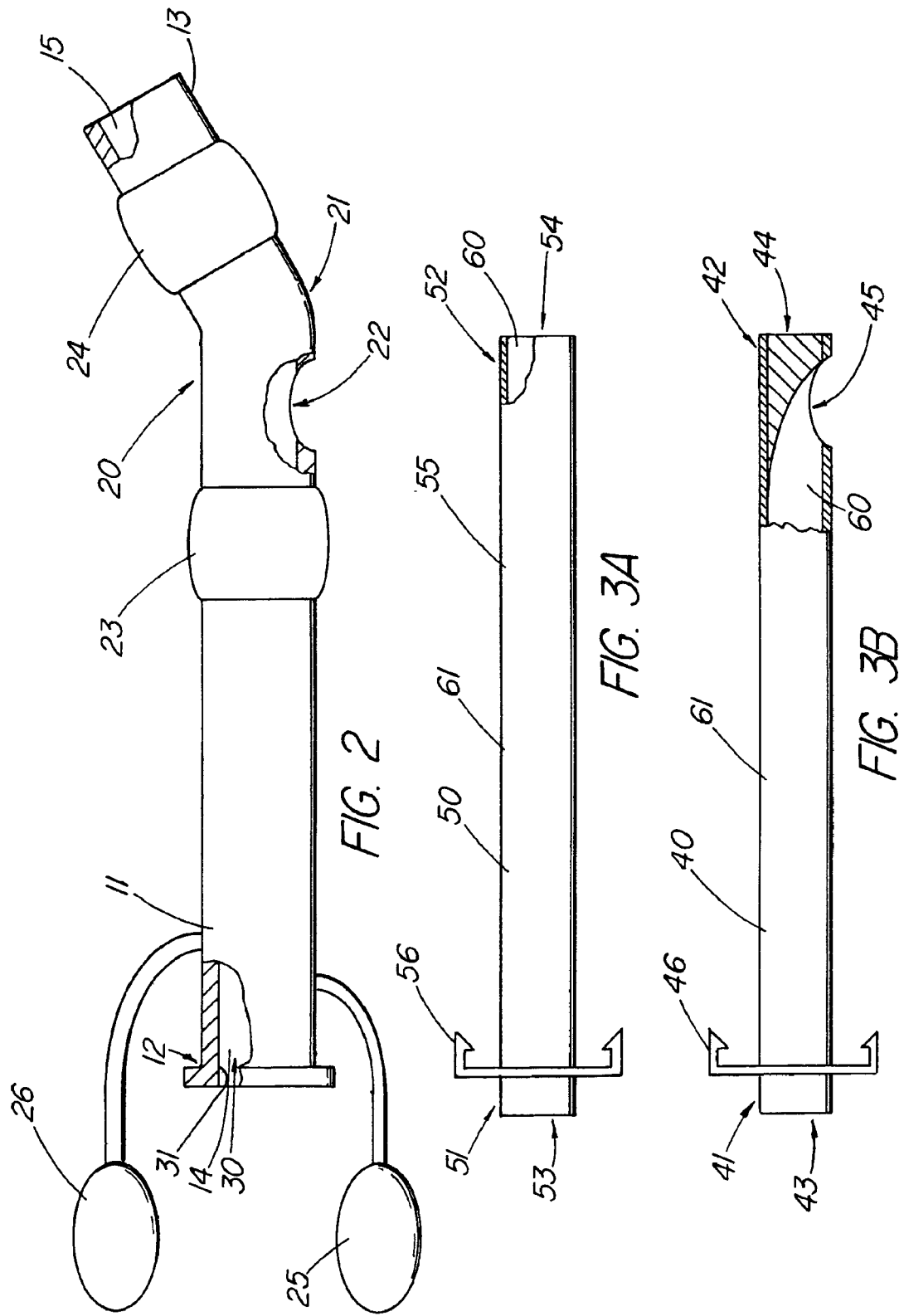

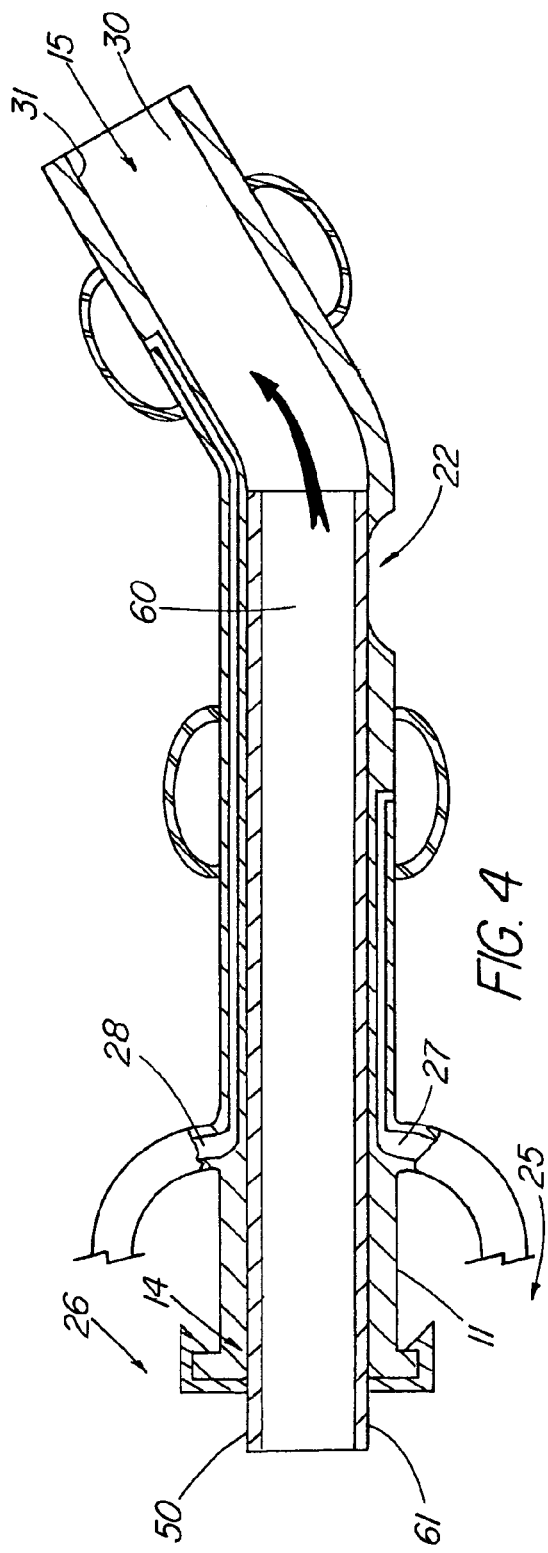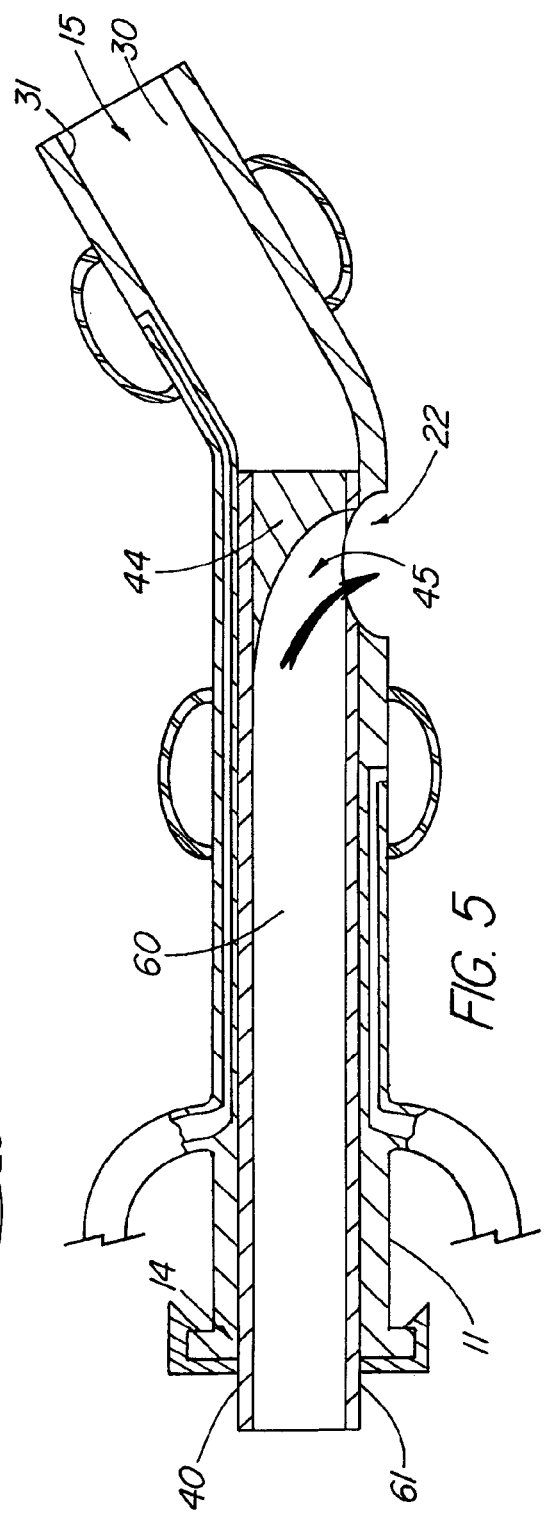

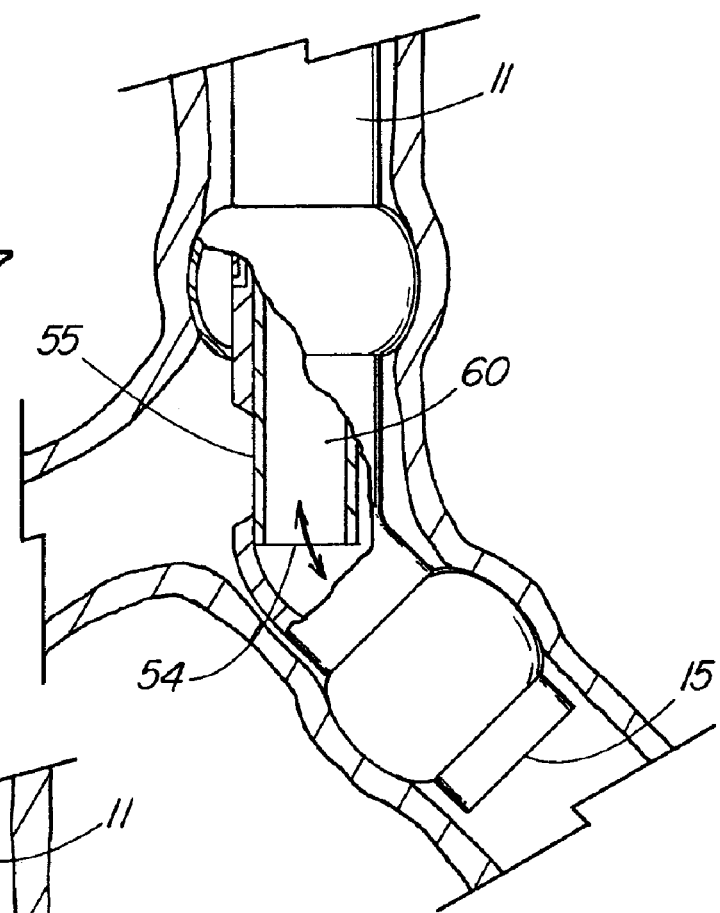
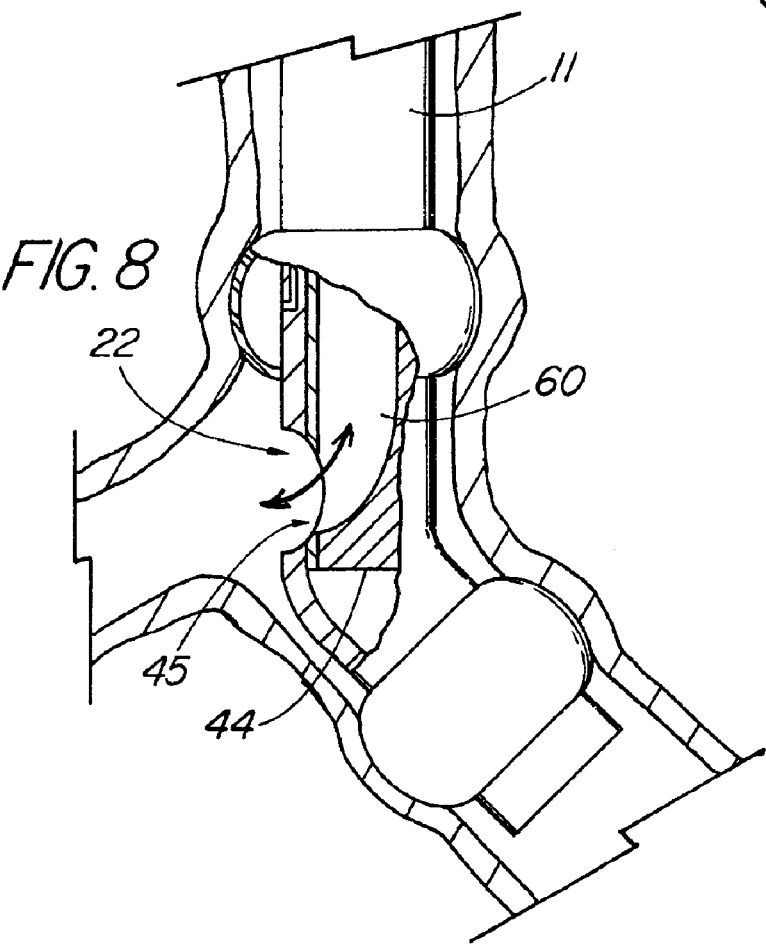

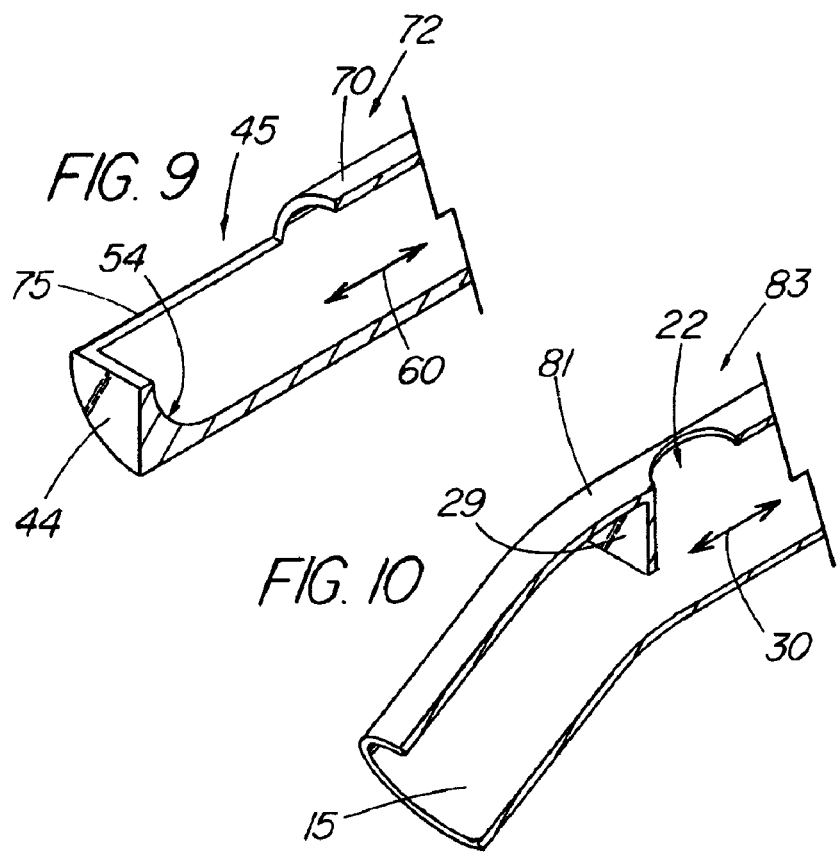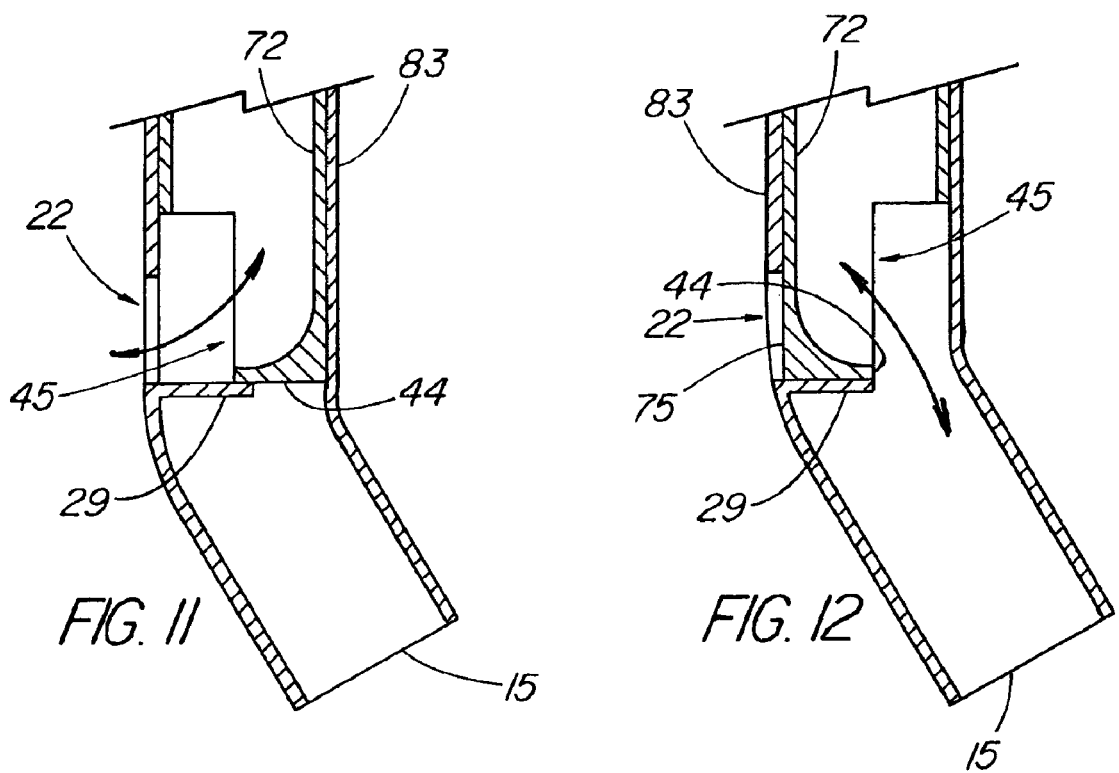

MEDICAL DEVICES AND METHODS OF SELECTIVELY AND ALTERNATELY ISOLATING BRONCHI OR LUNGS

RELATED APPLICATIONS

The present patent document claims the benefit of the filing date under 35 U.S.C. § 119(e) of provisional U.S. Patent Application Ser. No. 60/553,763, filed on Mar. 17, 2004, which is hereby incorporated by reference in its entirety.

FIELD OF THE INVENTION

The present invention relates to medical devices, and in particular to medical devices, kits, and methods of selectively and alternately isolating bronchi or lungs.

BACKGROUND OF THE INVENTION

Animals require a supply of oxygen for cellular respiration, and they must expel carbon dioxide, the waste product of this process. As such, a major function of the circulatory system is to transport and exchange gases such as oxygen and carbon dioxide between respiratory organs and other parts of the body.

Most land animals have respiratory organs (a pair of lungs in humans) folded within their body and restricted to a location within a thoracic cavity, also known as the chest wall, where they are protected by the thoracic vertebra. Because the pair of lungs is not in direct contact with the oxygen in the environment, a structure is needed to bring oxygen to the respiratory surface of the lungs and carry carbon dioxide away from the lungs. The structure here includes the mouth and the nose (the pharynx and the nasal cavity, respectively) where air is inhaled, passes through the larynx, and down the trachea commonly referred to as the windpipe.

The trachea is a cartilaginous and membranous tube for carrying gases such as air (hence the name windpipe). It is nearly but not exactly cylindrical, as it is somewhat flattened dorsally while being rounded ventrally. Approximately at the fifth thoracic vertebra, the trachea divides into a pair of bronchi, the right bronchus and the left bronchus corresponding and leading to the right and left lungs, respectively.

The right bronchus is wider, shorter, and less abrupt in its divergence (i.e., more of a straight shot) from the trachea than the left bronchus. The right bronchus gives rise to three subsidiary bronchi: the superior (upper), middle, and inferior (lower) lobes. The left bronchus gives rise to superior and inferior lobes. Each of the lobes of the right and left bronchi divides into still yet further branches. In contrast to the right bronchus, the left bronchus is smaller in diameter but about twice as long as the right, and it has a more abrupt divergence (is more offset) from the longitudinal axis of the trachea.

During lung surgery or other health care procedures, it may be desirable at times for the health care professional to isolate one of the pair of lungs. Here, "isolate" includes but is not limited to any of the following, similar, or related techniques with any one of the pair of bronchi or lungs: intubating, occluding, deflating/collapsing, suctioning, anesthetizing, ventilating, and reinflating. For illustrative purposes only, and not by way of limitation or exclusion, a few medical procedures where health care professionals may be called on to isolate one of the lungs might occur during lung biopsy, pulmonary resection, pneumonectomy, thoracotomy, pulmonary hemorrhage, hemoptysis, bronchopleural fistula, postoperative dehiscence of a mainstem bronchial stump, non-pulmonary thoracic aortic and esophageal surgery, lobectomy, bronchial surgery, and lung transplantation.

For instance, physicians may desire to anesthetize or stop ventilation to the lung that is about to undergo operation, diagnosis, or therapy. Furthermore, physicians may desire to suction either lung in the event of any collection and secretion of bodily fluids, when, for instance, hemorrhage occurs as one example. Additionally, physicians may resuscitate the anesthetized or non-ventilated lung. While the isolated lung undergoes medical procedures, the uninvolved lung is ventilated with oxygen for the patient.

A number of devices have been developed to facilitate lung isolating techniques, including endobronchial tubes, bronchial blockers, and double-lumen tubes. However, present devices and procedures might require a scope for guiding and placing the device. Also, these devices and procedures may be time consuming, difficult to position, require a balloon to be placed carefully in the opening to a bronchus or careful positioning of a slot, resulting in malposition or migration into the trachea, require repositioning as the operator alternates procedures between lungs, and may have a large overall outer diameter. In addition, these devices may require removal of the device or withdrawal of a component of the device from one bronchus to the other bronchus so as to selectively and alternately isolate bronchi or lungs.

Through the present devices, kits, and methods, isolating techniques such as intubating, occluding, deflating/collapsing, suctioning, anesthetizing, ventilating, and reinflating, and the like can be performed. Also, the devices of the present invention can be placed without the need for a scope. In addition, the present invention is easier to position, which saves time for the patient and health care professional. The smaller outer diameter is easier to place and better tolerated by the patient than the double lumen devices. Furthermore, the device goes into one bronchus, such as the left bronchus because it is easier for placing devices than the right, or either bronchus. Blocking of either bronchus is easier with the present device. By exchanging inner cannulas (or rotating/turning an inner member), isolation of either lung selectively and alternately can be achieved without repositioning the device between the bronchi or removal of the device from the patient. Also, swapping inner cannulas (or rotating/turning the inner member) is easier than positioning a balloon to occlude a bronchus.

Therefore, it is desirable to have devices, kits, and methods of isolating lungs or bronchi as taught herein.

SUMMARY OF THE INVENTION

A lung isolating device is provided. In one embodiment, the device comprises a main body having proximal and distal ends and defining a lumen, and having a side port and an opening formed near the distal end. An insert, separable from the main body and having first and second ends, is configured to be placed within the lumen of the main body, whereby the second end of the insert is positioned axially intermediate the proximal and distal ends of the main body. The insert has an aperture at or near each of its ends. The aperture at the second end selectively and alternately communicates with the main body side port or distal opening to allow a passageway through the insert and external to the main body to isolate one or the other bronchi or lungs.

In another embodiment, the lung isolating device according to the invention comprises a tubular member defining a channel in communication with openings at first and second ends of the tubular member and having a passageway formed intermediate the first and second ends. The tubular member has at least one cuff formed in a distal section at or near the distal end. A cannula is separable from and disposable in the channel intermediate the first and second ends of the tubular member, and is configured to detachably engage the first end of the tubular member. The cannula has an elongated shaft defining a lumen from an open proximal end to an orifice formed in a distal end to allow passage through the lumen and orifice of the cannula and out the tubular member to a bronchus or lung external the device.

In another embodiment, a lung isolating device according to the invention comprises an outer member having openings at proximal and distal ends and defining a channel. The outer member has a side port and a flange disposed proximal to the distal opening. An inner member is positioned within the outer member between first and second positions. The inner member has an opening at a first end, an aperture at a second end, a side orifice proximal to the aperture, and a lumen in communication with the opening, orifice, and aperture, whereby the inner member is configured to be positioned axially into the channel with the second end located proximal to the outer member flange. The outer member may be rotatably or otherwise switched from one position that allows passage through the side orifice of the inner member and out the side port of the outer member and out of the device to one of a pair of bronchi or lungs, and may be moved to the second position that allows passage through the inner member second end aperture and out the outer member distal opening and out of the device to the other bronchi or lung.

The present invention also comprises kits useful in isolating lungs. The kits include a main body having first and second ends and defining a channel in communication with a side port and an opening formed near the distal end. The kits further include a plurality of inserts separable from the main body for selectively and alternately isolating the left or the right bronchi or lungs.

Methods of isolating lungs are also provided. In one embodiment, a method according to the invention comprises providing a main body having first and second ends, a first end opening and an opening formed near the second end defining a lumen. An insert is provided that has proximal and distal ends and a portal, the insert capable of being placed into the lumen. The main body second end is advanced through an airway and into a bronchus of a patient. The insert is placed into the lumen. The distal end of the insert is positioned axially intermediate the first and second ends of the main body with the insert portal in communication with the main body second end opening.

In another embodiment, a method according to the invention comprises providing a tubular member having first and second ends and defining a channel in communication with first and second end openings and a passageway formed intermediate the ends. Also provided is a cannula having proximal and distal ends defining a lumen in communication with an aperture capable of allowing passage through the lumen to a first lung and a barrier capable of occluding passage through the lumen to a second lung. The second end of the tubular member is placed through the mouth, down the trachea, and into a lobe of a bronchus. A cuff is inflated. The cannula is inserted into the channel. The distal end of the cannula is advanced axially to a position intermediate the first and second ends of the tubular member. Passage through the lumen to the second lung is blocked while allowing passage through the lumen to the first lung.

In another embodiment, a method according to the invention comprises providing a main body having an outer member with proximal and distal end openings and a side port and defining a channel. The main body further has an inner tubular member with first and second end apertures and a side orifice and defining a lumen. The inner member is positionable between first and second positions. The main body is placed into a lobe of a bronchus and a passage is provided through the lumen to a first lung and occluding passage through the lumen to a second lung.

BRIEF DESCRIPTION OF THE DRAWINGS

FIG. 1 provides side views of various components of a kit according to one embodiment of the present invention.

FIG. 2 provides a side view, partially sectioned, of a medical device according to one embodiment of the invention.

FIG. 3A provides a side view, partially sectioned, of a medical device according to one embodiment of the invention.

FIG. 3B provides a side view, partially sectioned, of an alternate embodiment of FIG. 3A.

FIG. 4 provides a longitudinal sectional view of a medical device according to the invention where a device according to one embodiment of FIG. 3A has been placed in a device according to one embodiment of FIG. 2.

FIG. 5 provides a longitudinal sectional view of a medical device according to the invention where a device according to one embodiment of FIG. 3B has been placed in a device according to one embodiment of FIG. 2.

FIG. 7 is a partial sectional view of FIG. 6 where a device according to one embodiment of FIG. 3A has been utilized to isolate a lung.

FIG. 8 is a partial sectional view of FIG. 6 where a device according to one embodiment of FIG. 3B has been utilized to isolate a lung.

FIG. 9 is a sectional partial view, broken way, of a medical device according to another embodiment of the invention.

FIG. 10 is a sectional partial view, broken way, of a medical device according to an alternate embodiment of FIG. 2.

FIG. 11 is a sectional partial view, broken way, of a medical device according to the invention where a device according to an embodiment of FIG. 9 has been placed in a device according to one embodiment of FIG. 10.

FIG. 12 provides an alternate view of FIG. 11 where the device according to an embodiment of FIG. 10 has been rotated.

DETAILED DESCRIPTION OF EMBODIMENTS

Figure 6:
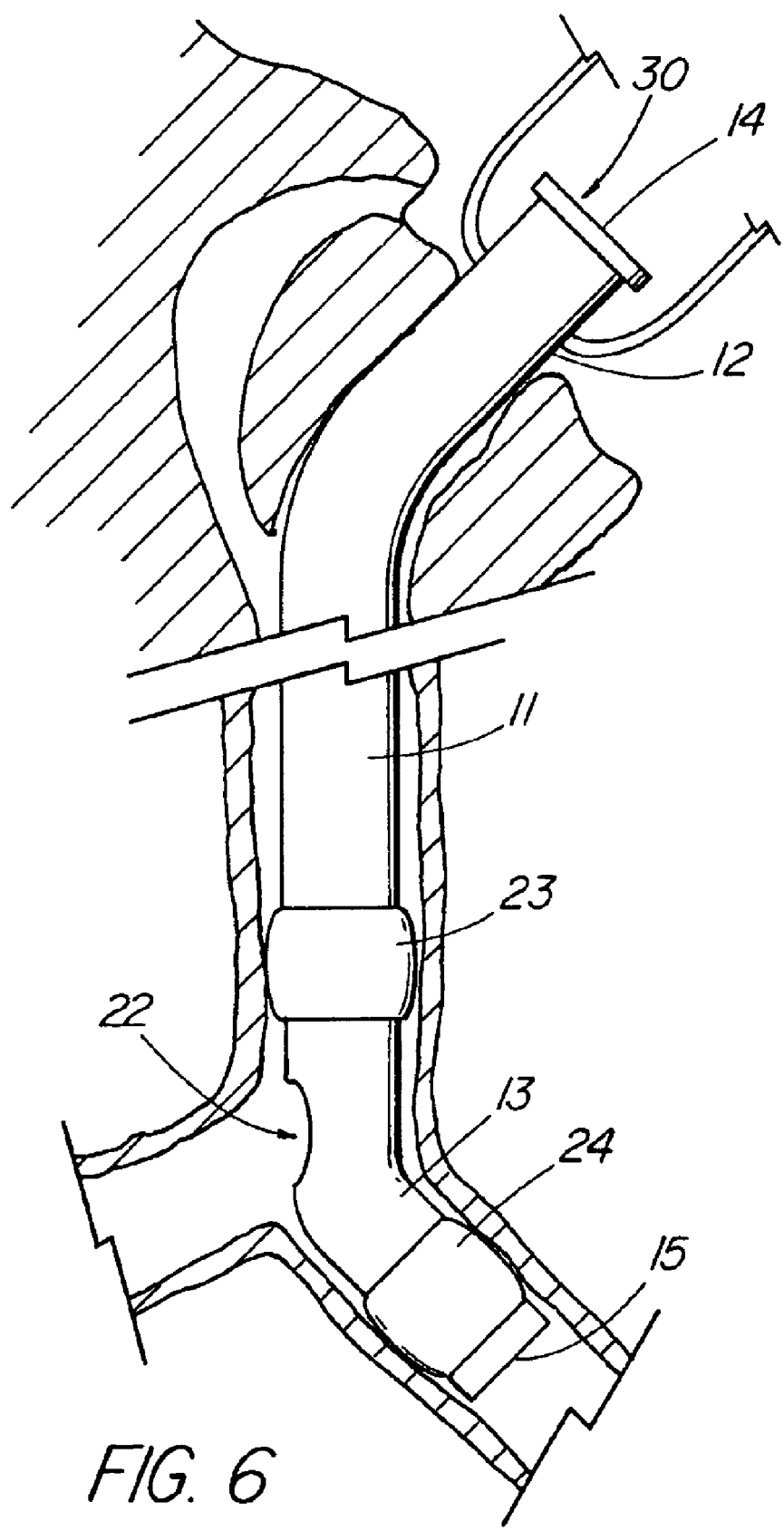
FIG. 6 is a diagrammatic side view, broken away, of an embodiment of a medical device where a device according to one embodiment of FIG. 2 has been advanced through a patient's mouth, trachea, and into a bronchial passage.

The present invention relates to medical devices, and in particular to medical devices, kits, and methods of selectively and alternately isolating bronchi or lungs. For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, with, contain(s) and the variants thereof are intended to be open ended transitional phrases, terms, or words that do not preclude the possibility of additional steps or structure.

As illustrated in FIG. 1, a lung isolating kit containing various components of one embodiment of the present invention is provided. In one embodiment, a kit 10 of an embodiment of the present invention comprises a main body 11. The kit further includes right and left inner inserts 40, 50.

Main Body

As shown in FIG. 2, the main body 11 has first (proximal) and second (distal) ends 12, 13, respectively, and a middle portion 20, and defining a lumen 30. As is conventional, "distal" means away from the operator when the device is inserted into a patient, while "proximal" means closest to or toward the operator when the device is inserted into a patient. By middle portion 20, it is understood that the section is intermediate the first and second 12, 13 ends. The term "intermediate," as used to describe embodiments of the invention, is intended to mean between, though not necessarily equidistant to, the distal-most tip of the second end 13 and the proximal-most tip of the first end 12. Furthermore, the section of the main body called the middle portion 20 is for the convenience of the reader viewing the drawings, but it could be considered a section of and thereby named as the second (distal) end 13 or the distal section. As used herein to describe embodiments of the invention, the term "lumen" is understood to be any chamber, channel, opening, bore, aperture, orifice, flow passage, passageway, or cavity that facilitates the conveyance, ventilation, flow, movement, blockage, evacuation, or regulation of gases such as air or oxygen in isolating one or both of the pair of lungs, the insertion of a cannula (insert), or the passage of a diagnostic, monitoring, scope, or other instrument (a "medical device").

The main body 11 may be made of any suitable material (natural, synthetic, plastic, rubber, metal, or combination thereof that is rigid, strong, and resilient, although it should be understood that the material may also be pliable, elastic, and flexible at the first end 12, second end 13, and middle portion 20. In certain embodiments of the invention, the main body may be flexible at the second end 13 and first end 12 and rigid at the middle portion 20. Alternatively, it may be flexible at the second end 13 and the middle portion 20 (or distal section) while the first end 12 and longer proximal section or center section of the middle portion 20 may be more or less rigid. In other embodiments, the first end 12 and proximal section of the middle portion 20 may be bendable.

FIG. 2 illustrates an embodiment of the main body 11 that is generally tubular. As used herein, the term main body comprises any "tubular." As used to describe embodiments of the invention, "tubular" includes any tube-like, cylindrical, elongated, shaft, round, oblong, or elongated structure or member that includes a lumen 30. Given the nearly cylindrical configuration of the trachea, a mostly rounded main body 11 may be better tolerated by the patient, although the main body may comprise other tubular configurations having a lumen 30, as when the cross-sectional view is generally square, rectangular, ovulate, or triangular as specific but non-limiting examples of embodiments that include a lumen 30. In one embodiment, the lumen 30 is defined by an inner wall 31 having an inner diameter. The inner wall 31 may be annula or tubular.

The main body 11 can be formed by any suitable means, including molding and shaping it onto a mandrel into a tubular configuration. Additionally, where a sheet is used to form the main body, features such as a side port 22 (explained below) may be stamped or cut away from the sheet before joining the edges (e.g., sides) of the sheet. Also, the main body and features of the main body may be machined, cut, milled, extruded, molded, or formed by any suitable means, and features may also be attached to the main body. In addition, the main body 11 may vary in length given the different sizes of the nasal cavities, pharynxes, larynxes, tracheas, and bronchi between men, women, and children. In certain embodiments of the invention, the main body 11 may be extendable at the proximal end 12, distal end 13, or middle portion 20.

Given the natural angle at which the left bronchus diverges from the longitudinal axis of the trachea, there is an elbow 21 at a distal section of the middle portion 20 of the main body 11 as shown in FIG. 2. Therefore, while the greatest length of the main body may be relatively straight in one embodiment, it may have a bend, curve, or angle to it at the elbow 21 configured for placement of the distal end 13 in the left bronchus. As a section of the main body 11, the elbow 21 may be pliable, elastic, and flexible as previously described.

As shown in FIG. 2, the main body 11 further comprises a side port 22 at the middle portion 20 (or distal section), a proximal opening 14 at the first end 12, and a distal opening 15 at the second end 13, whereby the side port 22 and the openings 14, 15 define a lumen 30. The term "side port" (side opening)—as used to describe embodiments of the invention—includes any structure that functions as a portal, port, passage, passageway, opening, hole, cutout, orifice, or aperture formed "intermediate" (as previously discussed) a distal/second end and a proximal/first end. As used to describe embodiments of the invention, the phrase "at or near" a distal/second end includes a location that is at, within, or a short distance to the distal-most end or distal section, that is closer to the distal/second end than the proximal/first end, located about the middle portion or distal section, or located distal to the side port (side opening).

There may be at least one cuff. FIG. 2 shows cuffs proximal and distal 23, 24, respectively, to the side port 22. In use, the distal cuff 24 is located in the left bronchus, while the proximal cuff 23 is located in the trachea above the bronchi. The distal cuff 24 is for sealing the air between the outside of the main body and the bronchus, while the proximal cuff 23 seals the air between the outside of the main body and the trachea.

Cuffs may be spherical in shape, or they may be elliptical in shape so as to better conform to the bronchial or tracheal walls when the cuffs are inflated. For example, cuffs may be any high volume, nonporous, low pressure bag so as to avoid compromising blood flow in the tracheal or bronchial walls and thereby presenting less risk of bronchial mucosal injury. One example of a cuff may be a balloon. The invention is not limited to balloons, spherical, or elliptical shapes, and it should be understood as being of or relating to any structure that can safely be inflated or deflated so as to form a seal against the inner walls of the bronchus or trachea. The cuffs can be inflated or deflated pneumatically by any suitable fluid. The term "fluid," as used to describe embodiments of the invention, is understood as including but not limited to air, water, oil, or a saline solution or other liquid or gas that is biocompatible or capable of being made biocompatible.

The proximal and distal cuffs 23, 24, respectively, are remotely, selectively, and communicatively coupled to controllers, such as for example proximal and distal input/output units 25, 26, respectively, by channels 27, 28, respectively. The input/output units 25, 26 may be connected to the main body at the hospital, ambulance, health care treatment location, or attached to the main body during manufacture. These fluid flow units 25, 26 regulate (control the amount, if any, of) the flow of fluid passing to the cuffs through any "duct," where the term duct—as used to describe embodiments of the invention—includes any structure, such as a channel, passageway, tube, or vessel, that functions to allow communication, conveyance, or flow of fluid to, from, associated with, or earmarked for a cuff. Input of fluids causes the cuffs to inflate and, thereby, sealably engage the inner walls of the tracheal or bronchial walls, while output of the fluids results in deflation of the cuffs and shrinkage away from the tracheal and bronchial walls.

The inner diameter of the inner wall 31 of the main body from the first end 12 to the elbow 21 is sufficient to accommodate the outer diameter of the outer wall 61 and placement of an "insert" 40, 50, respectively, such as and including a cannula, (discussed below). For example only and not by way of limitation, the inner diameter of the inner wall 31 of the main body may be approximately 15 millimeters, and the outer diameter could be slightly more than that.

The diameter of the insert and the main body need not be constant. Optionally as in certain embodiments of the invention, the inner diameter of the main body and insert may be tapered (reduced circumference) from the proximal end distally, although it should be understood that the circumferences may be constant, tapered, or a combination thereof. Also, the main body and insert may come in varying diameters given the different sizes of the nasal cavities, pharynxes, larynxes, tracheas, and bronchi between men, women, and children. The device includes a proximal opening 14 having an inner diameter sufficient to receive either of the cannulas separately.

Insert (Cannula)

The invention further comprises inserts. Generally stated, inserts (as used to describe embodiments of the invention) include any duct, vessel, tube, or structure defining a lumen and separable from and sized to be placed (including but not limited to being fitted, inserted, or nested) into the main body and configured to allow communication, discussed below, from the insert lumen to the main body distal (second) end opening or side port. Inserts include first and second ends and are configured with at least a side opening intermediate those ends or an opening at or near the distal end, which insert (cannula) opening communicates with a main body distal (second) end opening (or side port) to allow communication with a first lung/bronchus while occluding communication to a second lung/bronchus.

Examples of inserts include cannulas or tubular members. While subsequent discussion uses the term "cannula," it should be understood as a non-limiting example of a configuration of a tubular structure that performs the aforesaid insert function of selectively and alternately isolating lungs or bronchi.

Inner cannulas 40, 50 are illustrated in FIGS. 3A and 3B. A cannula is configured to be positioned longitudinally in an axial channel of the main body and containing a lumen 60 for communication with the main body. As used to describe embodiments disclosed herein, the term "communication" and variants thereof include the passage, conveyance, ventilation, flow, movement, blockage, occlusion, evacuation, or regulation of gases such as air or oxygen or anesthesia or secretion in isolating one or both of the pair of lungs, or the passage of a diagnostic, monitoring, scope, or other instrument (a "medical instrument"). In one embodiment, the cannulas 40, 50 are defined by an outer wall 61 having an outer diameter. The outer wall 61 may be annular or may be "tubular" as used to describe embodiments disclosed herein. The outer surfaces of the outer portion 61 of the cannula 40, 50 optionally face and are generally parallel to the surface of the inner wall 31 of the main body 11.

As shown in FIGS. 3A and 3B, the right and left cannulas 40, 50 are generally tubular with first ends 41, 51 and second ends 42, 52. Here, the term "left" cannula merely refers to the cannula that occludes the left bronchus or lung while allowing communication (e.g., passage, ventilation) to the right bronchus or lung. The term "right" cannula refers to the cannula that occludes the right bronchus or lung, while allowing communication (e.g., passage, ventilation) to the left bronchus or lung. Alternatively, the terms "left" and "right"—as used to describe embodiments of the invention—could be used to indicate the bronchus or lung that is being ventilated. Left bronchus (or lung) and right bronchus (or lung) is from the patient's stand point.

The length of each cannula is approximately the length of the main body 11. In one embodiment of the invention, the cannulas extend the length of the main body approximately to the elbow 21, while in another embodiment the cannulas stops just distal to the side port 22. The cannulas may be made of any materials suitable for the main body 11 and may be formed by any suitable means used to form the main body, discussed above.

As shown in FIG. 3A, the right cannula 50 has proximal and distal openings 53, 54, respectively, at or near its first and second ends 51, 52, respectively, and a sidewall 55 that blocks the side port 22 at the middle portion 20 of the main body 11. The distal opening 54 of the cannula communicates with the opening 15 of the main body to permit single lung isolation. As shown in FIG. 3B, the left cannula 40 has a proximal opening 43 at its first end 41 and a barrier 44 enclosing the second end 42 so as to occlude the passageway to the opening 15 at the distal end 13 of the main body 11. It should be understood that the term "occlude" and variants thereof—as used in describing embodiments of the invention—shall include but not be limited to any barrier 44 that obstructs, caps, blocks off, plugs, encloses, or closes up the passage to the opening 15 (or side port 22). The barrier 44 can be formed by any suitable means, such as a plug that is formed to fit securely in the lumen 60 at the distal end 42 of the left cannula 40. Alternatively, the barrier 44 can be attached to the distal end 42 of the left cannula 40 or the main body 11, which attachment may be carried out by any suitable means such as welding, brazening, sewing, adhesives, wires, chemical cross-linking, heat source, light source, radiofrequency, lasering, or other energy source for attaching the barrier 44 to the cannula or the main body. The barrier may also be a side wall, for example a side wall of the insert (cannula) in occlusion with the main body side port.

Also as shown in FIG. 3B, the left cannula 40 comprises a side opening 45 in communication with the side port 22 at the middle portion 20 of the main body 11. The side opening 45 may be any structure that may act as a counterpart to the main body side port, and includes for example a port, passage, passageway, opening, hole, cutout, orifice, or aperture formed at or near the main body side port or passageway.

A portal is formed near the second end 52, 42 of the insert (cannula) and the distal end 13 of the main body for selectively and alternately isolating one of a pair of bronchi or lungs. As used herein to describe embodiments of the invention, the term "portal" means any structure, including an inlet, outlet, lumen, chamber, channel, opening, bore, aperture, orifice, flow passage, passageway, or cavity, that permits "communication" between the cannula side opening 45 to the main body side port 22, or the cannula opening 54 to the main body distal opening 15. In other words, the portal may be an aperture at or near the second/distal end of the insert (cannula) and the side port or distal opening in the main body.

That is, a portal may be any connection or uniting of the cannula to the main body formed by the contiguous relationship (by touching, abutting, or nesting, by being near or in close proximity to, or by being adapted with a tube, gasket, or some other connector) of the distal opening 54 of the right cannula to the opening 15 of the main body, or the side port 22 of the main body and the side opening 45 of the left cannula, for facilitating the conveyance, ventilation, flow, movement, blockage, occlusion, evacuation, or regulation of gases such as air or oxygen or anesthesia in isolating one or both of the pair of lungs. Also, the side opening 45 and the side port 22 may be contoured so as to allow a diagnostic, monitoring, scope, or other instrument to pass through to the bronchus or lung.

As shown in FIGS. 3A and 3B, the first ends 41, 51, respectively, may also include securing members 46, 56, respectively, that detachably engage the proximal end 12 of the main body 11. For example, in certain embodiments of the invention the securing member 46 of the left cannula 40 may fit like a lock, and key to the first end 12 so as to ensure that the side opening 45 lines up and effectively communicates with the side port 22 at the middle portion 20 of the main body. In other embodiments, the securing member 56 of the right cannula 50 fits to the first end 12 of the main body 11 so as to ensure proper alignment of the opening 54 of the cannula and the distal opening 15 at the second end 13 of the main body. It is understood that securing members 46, 56 may be any structure for helping, controlling, or help preventing sliding movement of the cannulas with respect to the main body by clipping, gripping, clutching, or holding the cannulas to the main body.

The invention further comprises, as illustrated in FIGS. 4 and 5, that the inner cannulas 40, 50 are sized to be individually inserted into the opening 14 and lumen 30 of the main body 11. By the terms "inserted" or "insertion" it is understood that this includes any sliding, pushing, turning, rotating, or generally placing, disposing, or positioning either of the cannulas inside of the main body. In one embodiment, the separable cannulas 40, 50 upon insertion into the lumen 30 of the main body 11 are "placed." By the term "placed" it is meant that the combination of a cannula inside of the main body results in a single lumen device, that there is no or insubstantially little space or cavity or channel formed between the outer wall 61 of a cannula and the inner wall 31 of the main body. "Placed" may include fitted, and "nested."

The term nested (nest, nesting) includes a meaning whereby the inner surface of the inner wall 31 of the main body abuts the outer surface of the outer wall 61 of a cannula. Still further stated, the term nesting includes a meaning that the cannula fits concentrically, snugly, or compactly within the lumen 30 of the main body such that the lumen 60 of the cannula becomes the single lumen of the device for the various lung and bronchi isolating techniques (by way of example only, the conveyance, ventilation, flow, movement, blockage, evacuation, or regulation of gases such as air or oxygen or anesthesia in isolating one or both of the pair of lungs, the insertion of a cannula, or the passage of a medical instrument.

FIG. 4 shows the right cannula 50 inserted into the main body to block the side port 22 and permit passage through the opening 15. FIG. 5 shows the left cannula 40 inserted into the main body to obstruct the passage to the opening 15 and permit communication between the side opening 45 and the side port 22. Techniques such as (by way of example only) ventilation, suction, or conveyance of gases may be achieved in isolating one or both of the pair of lungs or bronchi, or the passage of a diagnostic, monitoring, scope, or other instrument for additional treatment of the patient.

FIG. 6 shows a schematic overview of the anatomy from the mouth and nose to the larynx and down the trachea to the left and right bronchi and lungs (not shown). In this embodiment of the invention, the lung isolating device includes a tubular main body 11 having proximal first and distal second ends 12, 13, respectively, having proximal and distal openings 14, 15, respectively, defining a lumen 30, a side passageway 22 located at or near the second end 13, and cuffs proximal and distal 23, 24, respectively, to the side port 22. In use, the main body proximal first end 12 extends outside the mouth of the patient while the main body distal second end 13 extends into the left bronchus of the patient, wherein the side passageway 22 is directed toward the right bronchus of the patient.

FIG. 7 is a closer view of the lower trachea and the divergence of the left and right bronchi. FIG. 7 further shows a partial sectional view of a main body 11 whereby an embodiment of a right cannula 50 according to FIG. 3A has been placed in the main body lumen. A cannula sidewall 55 blocks the side port passageway 22 of the main body 11 while a cannula aperture 54 is in communication to allow a passageway to the main body opening 15. In use, the main body 11 is shown having been advanced to the left bronchus and the right cannula has been positioned into the main body so as to occlude passage to the right lung (or bronchus) while allowing passage—shown by a double-headed arrow— through the lumen to the left lung (or bronchus). The cuffs have been inflated to provide a suitable seal to ensure that air does not pass to the right lung or bronchus.

In FIG. 8, an embodiment of a left cannula 40 according to the FIG. 3B has been used with the main body 11. The cannula 40 has a side opening 45 in communication with the main body side port 22, and a barrier 44 enclosing the cannula second end so as to occlude the passageway to the main body distal opening. In use, the main body 11 is shown having been advanced to the left bronchus and the left cannula has been positioned into the main body so as to occlude passage to the left lung (or bronchus) while allowing passage—shown by a double-headed arrow—through the lumen to the right lung (or bronchus). The cuffs have been inflated to provide a suitable seal to ensure that air does not pass to the left lung or bronchus.

FIG. 9 shows a partial view of an alternate embodiment of a second end of a cannula (insert). Here, there is an inner member 70 configured to serve the dual purpose of isolating either the left or right lung based on the inner member's rotation in relation to a main body. The inner member 70 has an opening at a first end (not shown) and a second end 72 and defining a lumen 60. In FIG. 9, a barrier 44 has been modified in a way that it is incomplete, so that the barrier 44 does not plug the entire second end 72 of the inner member 70 (i.e., the second end 72 of the inner member 70 has both a barrier 44 and an aperture 54 formed in it). This can be done, by way of example only and not by way of limitation, by having the barrier 44 shaped like a semicircle with the remainder of the circle being the aperture 54, or optionally, the barrier 44 may be shaped like a flange that protrudes toward the longitudinal axis of the inner member second end 72. Optionally, the lumen 60 side of the inner member barrier 44 may be configured to slope or ramp toward the aperture 54 so that there is a gradual, sloped, elliptical, or radial path toward the aperture 54 (which helps if a medical instrument is inserted). In the alternative, the barrier 44 may be relatively straight so that it is somewhat perpendicular to the lumen 60 side of the inner member.

In addition to the distal aperture 54, the inner member 70 also has a side orifice 45 proximal to the aperture 54. As will be shown, in a first position, the aperture 54 may be in communication with the main body second opening 15 while the distal end outer sidewall 75 occludes passageway to the main body side port 22. In a second position, the side orifice 45 is in communication with the main body side port 22 while the barrier occludes passageway to the main body distal opening 15.

FIG. 10 shows an alternate embodiment of an outer member 81 (e.g., main body). An outer member 81 according to this embodiment has an opening at a proximal end (not shown) and a distal end 83 and defining a lumen 30. In FIG. 10, the distal end 83 has a side port 22 and a distal opening 15. Also, this embodiment shows a flange 29 disposed intermediate the proximal and distal ends (although it could be placed at or near the distal end of the outer member). The flange 29 protrudes toward the longitudinal axis of the outer member distal end 82, wherein the flange 29 corresponds to the barrier 44 of the inner member 70. By way of example only, the flange 29 may be greater than—the diameter of the barrier 44 of the inner member 70, so that the outer member flange 29 overlaps and forms a seal with the inner member barrier 44 in order to occlude passage to the outer member distal opening 15.

FIGS. 11 and 12 show an embodiment of FIG. 9 positioned within an embodiment of FIG. 10 to provide a lung isolating device to selectively and alternately isolate a lung or bronchus. The inner member 70 is positioned axially within the channel 30 of the outer member 81 with the second end 72 of the inner member located proximal to the outer member flange 29. This positioning may be effected either during manufacture or via insertion during use by the health care professional. The inner member first end (not shown) is secured to the outer member proximal end (not shown) so that the inner member may be rotated between first and second positions to alternately and selectively isolate one of a pair of lungs.

In a first position shown in FIG. 11, the orifice 45 of the inner member second end 72 is aligned with the side port 22 of the outer member distal end 83 to allow passage (shown by a double-headed arrow) through the lumen and to a first bronchus or lung external to the outer member. The inner member second end 72 may be rotated or turned or otherwise moved to a second position as shown in FIG. 12, where the inner member second end orifice 45 is in communication with the outer member opening 15 at the outer member distal end to allow passage (shown by a double-headed arrow) through the lumen and to a second bronchus or lung external to the outer member. Optionally, the proximal end of the inner member may have indicators to inform the health care professional of the lung or bronchus being occluded or ventilated based on the position of the inner member 71 in relation to the outer member 81.

Methods

The invention also comprises methods of selectively and alternately isolating the bronchi or lungs.

Figure 13:
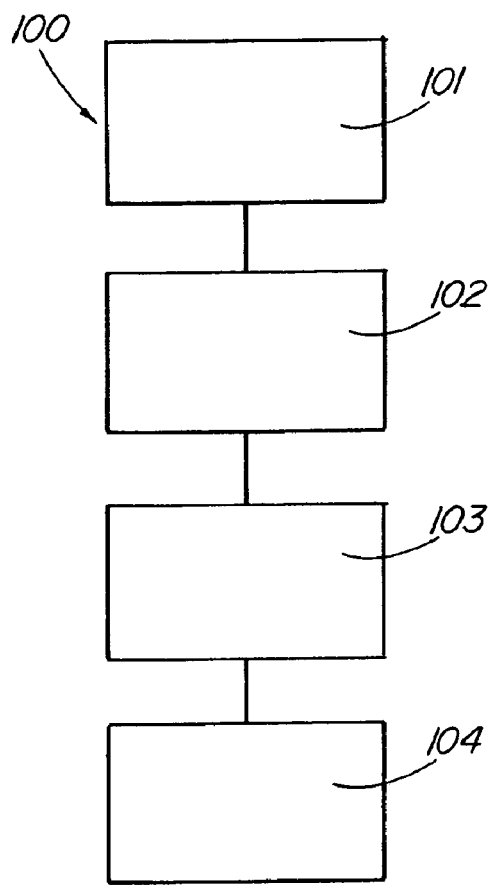
FIG. 13 is a block diagram illustrating a method of the invention.

As shown in FIG. 13, one embodiment 100 comprises providing a main body having first and second ends and defining a lumen, a first end opening, and an opening near the second end (step 101), whereby the opening may be at least a distal opening or a side port. The distal end of the main body is placed through the patient's mouth and positioned into the patient's left bronchus (step 102). The cuffs are then inflated (step 103). One of two individual inner cannulas (inserts) having proximal and distal ends and a portal is inserted Into the lumen of the main body axially intermediate the first and second ends of the main body with the cannula portal in communication with the main body distal opening to isolate, selectively and alternatively, the side port or the distal opening of the main body (step 104). In an alternative method, the other cannula is inserted into the lumen of the main body (step 104), and as a further alternative method, isolating the lungs includes inserting a first cannula for one lung, removing the cannula and inserting the second cannula for isolating the other lung (step 104).

A method of isolating a lung does not need to be performed sequentially. For example, the cuffs may be inflated (step 103) before or after either of the individual cannulas is inserted (step 104) into the main body. Likewise, a cannula may be inserted (step 104) into the main body outside of the patient (step 101) and before the main body is positioned (step 102) into the patient, or it may be inserted (step 104) after the main body has been placed (step 102) into the patient.

Figure 14:
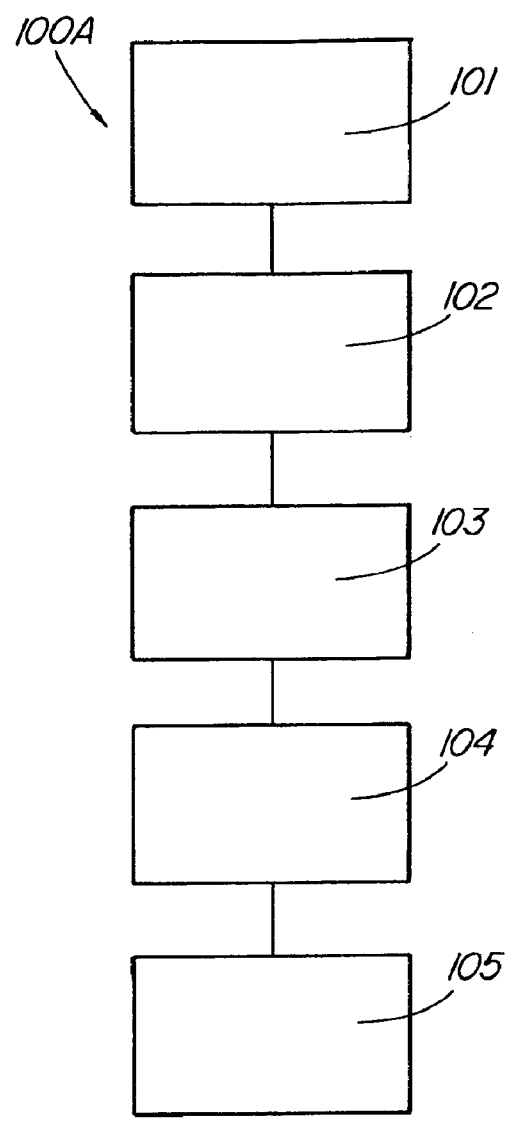
FIG. 14 is a block diagram illustrating another method of the invention.

In still another method 100A, as illustrated in FIG. 14, diagnostic, monitoring, scope, or other instrument may be introduced (step 105) through the cannula that has been inserted (step 104) into the main body. By way of example only, the other device may be a scope, respirator, ventilator, biopsy device, polyp grabber, nebulizer, catheter, stent, aspirator, dissector, resection device, scissors, forceps, suturing instrument, clamping device, suctioning instrument, or drug delivery instrument to name a few.

In yet another method of isolating selectively and alternately isolating lungs, a main body having a rotatable inner tubular member defining a lumen and an outer tubular member with first and second ends is provided. The main body is placing through the mouth, down the trachea, and into a lobe of a bronchus. Rotating or turning the inner member to a first position provides passage through the lumen to a first lung or bronchus and occludes passage through the lumen to a second lung or bronchus, while rotating or turning the inner member to a second position provides passage through the lumen to the second lung or bronchus while occluding passage through the lumen to the first lung.

In use, once the distal end of the main body is positioned in the left bronchus, the physician may selectively block and ventilating the left and right lungs, alternately, by inserting one of two inner cannulas into the lumen of the main body. As described above, each inner cannula is configured with a port and a solid portion that correspond to either the side port or the distal opening of the main body. Thus, selectively and alternately isolating one of the pair of lungs is achieved by the simple exchange of one cannula for the other, without removing the main body.

It is intended that the foregoing detailed description of the medical devices and methods of isolating bronchi or lungs be regarded as illustrative rather than limiting, and that it be understood that it is the following claims, including all equivalents, that are intended to define the spirit and scope of this invention. Terms are to be given their reasonable meaning; for instance, lung isolation and bronchi isolation may be used interchangeably in that blocking ventilation to the left bronchus includes in the broadest sense a resulting occlusion of the left lung. This may be called left bronchus or left lung isolation. Therefore, the embodiment of any figure and features thereof may be combined with the embodiments depicted in other figures. Other features known in the art and not inconsistent with the structure and function of the present invention may be added to the embodiments.

While particular elements, embodiments and applications of the present invention have been shown and described, it will be understood, of course, that the invention is not limited thereto since modifications may be made by those skilled in the art, particularly in light of the foregoing teachings. For example, embodiments may include a nested cannula slidably positioned in the lumen of the main body, where the side opening 45 remains in communication with the side port 22 at the middle portion 20 of the main body 11. Furthermore, while the device preferably goes in the left bronchus, which is easier to place than devices that go in the right bronchus or both bronchi, the main body could be inserted into the right bronchus by straightening the elbow 21 (or by positioning the elbow and having the side port 22 opening into the left bronchus, with the cannula 50 now allowing passage to the right lung while blocking the left, and the cannula 40 allowing passage to the left lung while blocking the right. Therefore, it is therefore contemplated by the appended claims to cover such modifications as incorporate those features which come within the spirit and scope of the invention.

What is claimed is:

1. A device adapted for isolating one of a patient's lungs, comprising:
   a main body having proximal and distal ends and defining a lumen, the main body having a side port and an opening formed near the distal end; and
   an insert separable from the main body and configured to be placed within the main body lumen, the insert having first and second ends, the second end positioned axially intermediate the proximal and distal ends of the main body, and an aperture at or near the first end and an aperture at or near the second end, wherein the insert second end aperture is in fluid communication with one of the main body side port and distal end opening for isolating one of said lungs.

2. The device of claim 1 wherein the side port is formed intermediate the main body proximal and distal ends.

3. The device of claim 1 wherein the insert is a cannula.

4. The device of claim 1 wherein the second end insert aperture is in communication with the main body side port.

5. The device of claim 4 wherein the second end of the insert further comprises a barrier in occlusion to the main body distal opening.

6. The device of claim 1 wherein the second end insert aperture is in communication with the main body distal opening.

7. The device of claim 6 wherein the second end of the insert further comprises a sidewall in occlusion to the main body side port.

8. The device of claim 1 wherein the insert further comprises a securing member to detachably engage the main body.

9. The device of claim 1 wherein the main body further comprises a cuff.

10. The device of claim 9 wherein the main body further comprises a fluid flow channel in communication with the cuff.

11. The device of claim 10 further comprising a fluid flow controller in communication with the channel.

12. A device adapted for isolating one of a patient's lungs, comprising:
   an outer member having openings at proximal and distal ends and defining a channel, the outer member having a side port and a flange disposed proximal to the distal opening; and
   an inner member positioned within the outer member between first and second positions, the inner member baying an opening at a first end, an aperture at a second end, a side orifice proximal to the aperture, and a lumen in communication with the opening, orifice, and aperture, wherein the inner member is positioned axially into the channel with the second end located proximal to the outer member flange, wherein in the first position the inner member aperture is in fluid communication with one of the outer member distal opening and flange for isolating one of said lungs.

13. The device of claim 12 wherein in the first position the orifice of the inner member is in communication with the side port of the outer member.

14. The device of claim 13 wherein the aperture overlaps the flange and comprises an occlusion to the outer member distal opening.

15. The device of claim 12 wherein in the second position the aperture of the inner member is in communication with the distal opening of the outer member.

16. The device of claim 15 wherein a sidewall of the inner member comprises an occlusion to the side port of the outer member.

17. The device of claim 12 wherein the outer member further comprises a cuff.

18. The device of claim 17 wherein the outer member further comprises a channel in communication with the cuff.

19. The device of claim 18 further comprising a controller in communication with the channel.

20. A kit adapted for selectively and alternately isolating one of a patient's lungs, comprising:
   a main body having first and second ends and defining a channel in communication with a side port and an opening formed near the second end; and
   a plurality of inserts separable from the main body, the inserts having proximal and distal ends defining a lumen, each of the plurality of inserts being sized to detachably insert into the channel, the distal end positioned axially intermediate the first and second ends of the main body, wherein the insert lumen is in fluid communication with one of the main body side port and second end opening for isolating one of said lungs.

21. The kit of claim 20 wherein one insert includes a side orifice in communication with the main body side port and a distal barrier that forms an occlusion to the main body second end opening.

22. The kit of claim 20 wherein one insert includes a distal orifice in communication with the main body second end opening and a side wall that forms an occlusion to the main body side port.

23. A method of selectively and alternately isolating lungs, comprising:
   providing a main body having first and second ends, a first end opening and an opening formed near the second end defining a lumen;
   providing an insert having proximal and distal ends and defining a lumen, a portal located at or near the distal end, the insert capable of being placed in the main body lumen;
   advancing the second end through an airway and into a bronchus of a patient;
   inserting the insert into the main body lumen; and positioning the distal end of the insert axially intermediate the first and second ends of the main body with the insert portal in communication with the main body second end opening.

24. The method of one of claim 23 further comprising providing a cuff to the main body and inflating the cuff.

25. The method of one of claim 23 further comprising securing the insert to the main body.

26. The method of claim 23 further comprising passing a medical device through the main body lumen.

27. A method of selectively and alternately isolating lungs, comprising:
providing a main body having an outer member having proximal and distal end openings and a side port and defining a channel;
providing an inner member having first and second ends, an aperture formed at each end, the apertures and a side orifice defining a lumen, the inner member positionable between a first position and a second position;
placing the main body into a lobe of a bronchus; and
positioning the inner member to the first position providing a passage through the lumen to a first lung and occluding passage through the lumen to a second lung.

28. The method of claim 27 further comprising rotating the inner tubular member in relation to the outer tubular member and allowing passage through the lumen to the second lung and occluding passage through the lumen to the first lung.

29. The method of claim 27 further comprising passing a medical device through the lumen.

* * * * *